United States Patent [19]

Bauer et al.

[11] 4,245,124
[45] Jan. 13, 1981

[54] ISOCAMPHYL-GUAIACOL-ETHYL ETHERS

[75] Inventors: Kurt Bauer; Gerd-Karl Lange, both of Holzminden, Fed. Rep. of Germany

[73] Assignee: Bayer Aktiengesellschaft, Leverkusen, Fed. Rep. of Germany

[21] Appl. No.: 71,432

[22] Filed: Aug. 30, 1979

[30] Foreign Application Priority Data

May 25, 1979 [DE] Fed. Rep. of Germany ....... 2921139

[51] Int. Cl.³ .................. C07C 43/205; C07C 43/21
[52] U.S. Cl. .................. 568/633; 568/820; 568/734
[58] Field of Search .................. 568/633, 820

[56] References Cited

U.S. PATENT DOCUMENTS

| | | | |
|---|---|---|---|
| 2,537,647 | 1/1951 | Kitchen | 568/633 X |
| 2,581,916 | 1/1952 | Kitchen | 568/633 X |
| 4,061,686 | 12/1977 | Hall et al. | 568/820 |
| 4,112,000 | 9/1978 | Mardigvian | 568/633 X |

FOREIGN PATENT DOCUMENTS 423058  4/1967  Switzerland .................. 568/820

OTHER PUBLICATIONS

Morrison et al., Organic Chemistry, 3rd Ed. (1973), 799–800.
Aul'chenko et al., Chemical Abstracts, vol. 68 (1968), 39823Q.

*Primary Examiner*—Bernard Helfin
*Attorney, Agent, or Firm*—Sprung, Felfe, Horn, Lynch & Kramer

[57] ABSTRACT

The invention concerns to new (isocamph-5-yl)-guaiacyl ethers of the formula

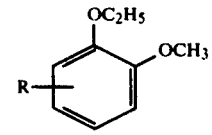

wherein R is an isocamph-5-yl radical in the 6- or 4-position relative to the ethoxy group;

a process for their preparation and their use for the preparation of 3-(isocamph-5-yl)-cyclohexanol which is an important constituent of sandal compound.

2 Claims, No Drawings

ISOCAMPHYL-GUAIACOL-ETHYL ETHERS

The present invention relates to (isocamph-5-yl)-guaiacyl ethers of the formula

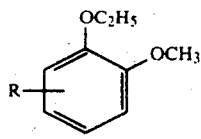

in which R represents an isocamph-5-yl radical in the 6- or 4-position relative to the ethoxy group.

The invention further relates to a process for the preparation of the ethers of the formula (I). The process is characterised in that 6- or 4-(isocamph-5-yl)-guaiacol, in the form of its alkali metal salts, is alkylated with an ethyl halide or with diethyl sulphate.

The invention further relates to the use of the ethers of the formula (I) or of their mixtures for the preparation of 3-(isocamph-5-yl)-cyclohexanol.

Amongst the ethers according to the invention, of the formula (I), namely 6- and 4-(isocamph-5-yl)-guaiacyl ethyl ether, 4-(isocamph-5-yl)-guaiacyl ethyl ether is preferred.

To prepare the ethers according to the invention, of the formula (I), 6- or 4-(isocamph-5-yl)-guaiacol, or mixtures of the two compounds are converted to the alkali metal phenolate by means of an alkali metal hydroxide, especially sodium hydroxide or potassium hydroxide, an alkali metal alcoholate, especially sodium ethylate or potassium ethylate, or alkali metal carbonates, especially potassium carbonate. Where an alkali metal hydroxide is used, the alkylation is carried out preferably in aqueous solutions by means of diethyl sulphate, where an alkali metal alcoholate is used the alkylation is carried our preferably in the corresponding alcohol by means of ethyl iodide, ethyl bromide or diethyl sulphate, and where potassium carbonate is used, the alkylation is preferably carried out in acetone, by means of diethyl sulphate.

The mixtures of 6- and 4-(isocamph-5-yl)-guaiacol which may be used can also be the reaction products obtained, for example, from the condensation of camphene with guaiacol. These reaction products predominantly consist of the two guaiacols mentioned. The other compounds contained in the reaction products do not interfere with the etherification reaction.

The reaction of 6- and 4-(isocamph-5-yl)-guaiacol with diethyl sulphate in the presence of potassium carbonate in acetone has proved particularly advantageous.

Isocamph-5-yl-guaiacol and the alkali metal hydroxide or alcoholate are advantageously employed in a molar ratio of 1:1-5, preferably 1:1-3. The alkylating agent is employed in an amount of 1.2 to 4 mols, preferably 1.25 to 3 mols, per mol of isocamph-5-yl-guaiacol.

The alkylation is advantageously carried out at 0° to 80° C., preferably 30° to 60° C.

For further conversion to 3-(isocamph-5-yl)-cyclohexanol, the ethers according to the invention, of the formula (I), are next partially cleaved to give 5- or 3-(isocamph-5-yl)-2-ethoxy-phenol.

The partial ether cleavage can be carried out with an alkali metal alcoholate in alcohol, for example sodium methylate or potassium methylate in methanol, or sodium ethylate or potassium ethylate in ethanol, in an autoclave at 130° to 200° C., preferably 150° to 180° C.

However, partial ether cleavage by means of a Grignard reagent, such as methyl-magnesium bromide or methyl-magnesium iodide, at temperatures of 100° to 160° C., preferably 120° to 140° C., is preferred.

The 5- or 3-(isocamph-5-yl)-2-ethoxy-phenol resulting from the partial ether cleavage of the ethers according to the invention, of the general formula (I), is then hydrogenated with hydrogen in the presence of Raney nickel, at a temperature of 180° to 210° C. and a pressure of 130 to 200 bar, to give 3-(isocamph-5-yl)-cyclohexanol.

The ethers according to the invention, of the formula (I), are valuable intermediates for the preparation of 3-(isocamph-5-yl)-cyclohexanol, an important constituent of sandal compound. Using these ethers, 3-(isocamph-5-yl)-cyclohexanol can be prepared substantially more economically than by the previously known processes.

The 2,4-dinitrophenyl ethers of 6- and 4-(isocamph-5-yl)-guaiacol, proposed in C.A. 68, (1968), 39823 z as intermediates for the preparation of 3-(isocamph-5-yl)-cyclohexanol, give 3-(isocamph-5-yl)-phenol, the last intermediate in the preparation of 3-(isocamph-5-yl)-cyclohexanol, in only about 50% yield, relative to 4-(isocamph-5-yl)-guaiacol. Using the ethers according to the invention, of the formula (I), 3-(isocamph-5-yl)-cyclohexanol is on the other hand obtained in up to 85% yield, relative to 4-(isocamph-5-yl)-guaiacol.

Furthermore, the ethers according to the invention are incomparably cheaper than the 2,4-dinitrophenyl ethers, the preparation of which requires 2,4-dinitrofluorobenzene, which is difficult to obtain and is expensive.

The process for the preparation of 3-(isocamph-5-yl)-cyclohexanol, proposed in German Auslegeschrift No. 1,223,482 is substantially less economical still than the process described in C.A. 68, (1968), 39823 z. It starts from terpenylphenols, which are converted, in a complicated multi-stage reaction, via terphenyl methyl ketones, into 3-(isocamph-5-yl)-cyclohex-2-en-1-one, which is then hydrogenated to 3-(isocamph-5-yl)-cyclohexanol. The yield in this process is not even 20%, relative to the terpenylphenol starting material.

EXAMPLE 1

A solution of 598 g (2.3 mols) of 4-isocamph-5-yl)-guaiacol in 2.3 l of acetone is mixed with 955 g (6.93 mols) of potassium carbonate and warmed to 50° C. 1,150 g (7.47 mols) of diethyl sulphate are then added dropwise in the course of one hour and after completion of the addition the mixture is boiled under reflux for 8 hours. It is then cooled, the potassium salt is filtered off and the solvent is distilled off. The residue is distilled in vacuo.

Yield: 622 g (=94% of theory) of 4-(isocamph-5-yl)-guaiacyl ethyl ether.

Boiling point: 150°-152° C./0.35 mm Hg.

If instead of 4-(isocamph-5-yl)-guaiacol, 598 g of a terpenyl-guaiacol mixture, obtained by reacting camphene with guaiacol in the presence of a Friedel-Craft catalyst, are employed, a terpenylguaiacyl ethyl ether mixture, which distils over at 163°-240° C./1 mm Hg, is obtained in a yield of 525 g (=79.3% of theory).

EXAMPLE 2

A solution of 396 g (1.375 mols) of 4-isocamph-5-yl)-guaiacyl ethyl ether in 500 ml of xylene is added dropwise to a freshly prepared solution of methyl-magnesium iodide in diethyl ether, prepared from 35 g (1.44 mols) of magnesium and 215 g (1.5 mols) of methyl iodide in 400 ml of diethyl ether. The diethyl ether is then distilled off. A further 500 ml of xylene are added in order to keep the reaction mixture in solution, and the batch is boiled under reflux for 8 hours. After it has cooled, 1 liter of 25% strength sulphuric acid is added, whilst cooling with ice. After adding 1 liter of toluene, the batch is mixed thoroughly and the aqueous phase is separated off. The organic phase is washed until neutral and the solvents are stripped off. The residue which remains is distilled.

Yield: 360 g (=95.5% of theory) of 5-(isocamph-5-yl)-2-ethoxy-phenol.

Boiling point: 147°–150° C./0.4 mm Hg.

If instead of 4-(isocamph-5-yl)-guaiacyl ethyl ether, 396 g of the terpenyl-guaiacyl ethyl ether mixture are employed, 361.5 g (=95.9% of theory) of a terpenyl-ethoxy-phenol mixture, which distils over at 144°–173° C./0.7 mm Hg, are obtained.

EXAMPLE 3

300 g (1.09 mols) of 5-(isocamph-5-yl)-2-ethoxy-phenol are hydrogenated in the presence of 30 g of Raney nickel at 200° C. under a hydrogen pressure of 155 atmospheres. The absorption of hydrogen has ceased after 20 hours. After adding 1 liter of carbon tetrachloride, the catalyst is filtered off and the filtrate is freed from the solvent. The residue is distilled.

Yield: 243 g (=94.2% of theory) of 3-(isocamph-5-yl)-cyclohexanol (cis-trans isomer mixture).

Boiling point: 130°–135° C./0.2 mm Hg.

If instead of 5-(isocamph-5-yl)-2-ethoxy-phenol, 300 g of the terpenyl-ethoxy-phenol mixture are employed for the hydrogenation, 244 g (=94.6% of theory) of a terpenylcyclohexanol mixture, which distils over at 132°–171° C./1 mm Hg, are obtained.

What is claimed is:

1. (Isocamph-5-yl)-guaiacyl ethers of the formula

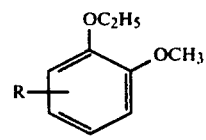

wherein
R is an isocamph-5-yl radical in the 6- or 4-position relative to the ethoxy group.

2. 4-(Isocamph-5-yl)-guaiacyl ethyl ether.

* * * * *

UNITED STATES PATENT AND TRADEMARK OFFICE
CERTIFICATE OF CORRECTION

PATENT NO. : 4,245,124
DATED : Jan. 13, 1981
INVENTOR(S) : Kurt Bauer et al.

It is certified that error appears in the above—identified patent and that said Letters Patent is hereby corrected as shown below:

On the title page, Assignee , "Bayer Aktiengesellschaft, Leverkusen, Germany" should read -- Haarman & Reimer GmbH, Holzminden, Germany --.

Signed and Sealed this

*Twenty-fourth* Day of *November 1981*

[SEAL]

*Attest:*

*Attesting Officer*

GERALD J. MOSSINGHOFF

*Commissioner of Patents and Trademarks*